United States Patent [19]

Gasperina

[11] Patent Number: 5,491,781
[45] Date of Patent: Feb. 13, 1996

[54] METHOD AND APPARATUS FOR DISPLAYING A GRAPHIC IMAGE

[75] Inventor: Marco D. Gasperina, Tigard, Oreg.

[73] Assignee: Hewlett-Packard Company, Palo Alto, Calif.

[21] Appl. No.: 31,780

[22] Filed: Mar. 12, 1993

[51] Int. Cl.⁶ ........................................................ G06F 3/14
[52] U.S. Cl. ............................................ 395/157; 395/155
[58] Field of Search ..................................... 395/155, 157, 395/159, 161, 164, 135, 275, 162; 364/710, 14

[56] References Cited

U.S. PATENT DOCUMENTS

| | | | |
|---|---|---|---|
| 4,914,568 | 4/1990 | Kodosky et al. | 395/275 |
| 5,062,060 | 10/1991 | Kolnick | 395/159 |
| 5,317,686 | 5/1994 | Salas et al. | 395/159 |
| 5,333,247 | 7/1994 | Gest et al. | 395/155 |
| 5,339,391 | 8/1994 | Wroblewski et al. | 395/157 |
| 5,353,391 | 10/1994 | Cohen et al. | 395/135 |
| 5,371,851 | 12/1994 | Pieper et al. | 395/164 |
| 5,388,202 | 2/1995 | Squires et al. | 395/157 |

*Primary Examiner*—Raymond J. Bayerl
*Assistant Examiner*—Ruay Lian Ho

[57] ABSTRACT

A selected portion of a graphical image is displayed in a window on a monitor. A scroll box on one side of the window is provided for changing the displayed portion of the image responsive to the movement of the scroll box. The scroll box includes end portions, or handles, which may be dragged to resize the scroll box. This has the effect of changing the scale or magnification of the displayed portion of the image. In the preferred embodiment, the invention is implemented in a Windows™ computer environment. Resizable scroll boxes, as described, may be provided for both horizontal and vertical dimensions of the display window. The described user interface has the advantage of providing an integrated control for both selecting a portion of the graphical image for viewing and selecting the scale of the viewed portion in an intuitive manner.

23 Claims, 3 Drawing Sheets

METHOD AND APPARATUS FOR DISPLAYING A GRAPHIC IMAGE

BACKGROUND OF THE INVENTION

1. Field of the Invention

The present invention relates generally to methods and apparatus for displaying a selected portion of a graphical image in a window on a monitor and more particularly to methods and apparatus in which a scroll box on one side of the window is provided for changing the displayed portion of the image responsive to movement of the scroll box.

2. Description of the Related Art

Scroll boxes are commonly used for locating and displaying a portion of a file in windowing programs such as Microsoft Windows™ and MOTIF™. A scroll bar indicates the possible areas to be viewed and a scroll box position on the scroll bar indicates the position of that portion of the file in the window relative to the total file length. For example, in a word processing program if the scroll box is halfway down the scroll bar it indicates that the screen is displaying a portion from approximately the middle of the document. In some such programs, the size of the scroll box changes relative to the scroll bar to indicate a percentage of the displayed portion of the image relative to the entire image. In other words, the scroll bar is proportional to the length of the entire image and the scroll box is proportional to the length of the displayed image.

In such a system an operator uses a mouse to position the cursor on the scroll box, depresses a button on the mouse, and moves the mouse thereby moving the scroll box so long as the mouse button is depressed. Such mouse movement moves the box relative to the scroll bar. When the mouse button is released a new portion of the file corresponding to the new scroll box position is displayed in the window.

Often, graphical images, such as data in the form of graphs are displayed in a window formed on a monitor by a computer. For example, a patient may be fitted with an heart rate recorder which records heart rate waveforms generated by the patient for predetermined period of time. Typically the time period is 24 hours. The recorded data is played back and stored in the computer memory for display in a window formed on a monitor as described above.

Such a graph must be manipulated in order to change the scale, e.g., "to zoom in" to a particular portion of the graph to reveal details or to "zoom out" to observe an overall pattern. The scale of the graph and the portion being viewed are independent parameters. By analogy, if the graph were printed on paper, a magnifying glass could be positioned over the paper. The height of the magnifying glass controls the magnification while the lateral and longitudinal positions of the glass determine which portion of the graph is viewed. When a graph is displayed on a computer monitor, separate controls are used to select a portion of the graph for viewing and to select the scale of the viewed portion.

It would be desirable to provide an integrated control for selecting a portion of the graphical image for viewing and for selecting the scale of the viewed portion.

SUMMARY OF THE INVENTION

The present invention comprises a method for displaying a portion of a computer file. A selected portion of the file is displayed in the window having a scroll box on one side. The scroll box is operable to vary the portion of the file displayed in the window. When a user changes the length of the scroll box, the scale of the displayed portion of the file changes proportional to change the length of the scroll box.

Apparatus is also provided for performing the method.

It is a general object of the present invention to provide an integrated control for selecting a portion of a file displayed in a window on a monitor controlled by a computer and for selecting the scale of the displayed portion.

It is another object of the present invention to provide such a method and apparatus in which the scale of the displayed portion is controlled by changing the length of the scroll box responsive to dragging one end of the scroll box with a cursor.

The foregoing and other objects, features and advantages of the invention will become more readily apparent from the following detailed description of a preferred embodiment which proceeds with reference to the drawings.

BRIEF DESCRIPTION OF THE TABLES

TABLE 1 are graph control configuration messages.

TABLE 2 are graph control status messages.

TABLE 3 are user interaction event messages.

TABLE 4 are graph control software state variables.

DETAILED DESCRIPTION OF THE PREFERRED EMBODIMENT

Figure 1A:
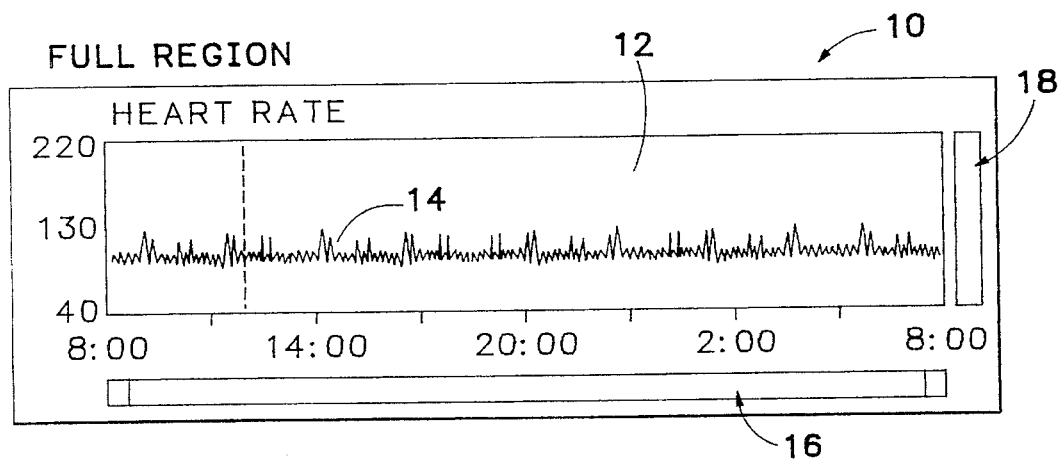
FIG. 1A illustrates a window having a complete heart rate wave form image displayed therein

Turning now to FIG. 1A indicated generally at 10 is a display formed on a CRT screen incorporated into a system constructed in accordance with the present invention. The present embodiment of the invention comprises a personal computer having an Intel™ 386 central processor, a keyboard, a color VGA monitor, a mouse and a Microsoft Windows™ graphical user interface. The computer is programmed, in a manner which is described in more detail hereinafter, to operate in accordance with the following description of the preferred embodiment.

Prior to describing the manner in which the computer program, controls the system, a description will first be made of the user interface and the manner in which the present embodiment is used to display a heart rate wave form.

Figure 1B:
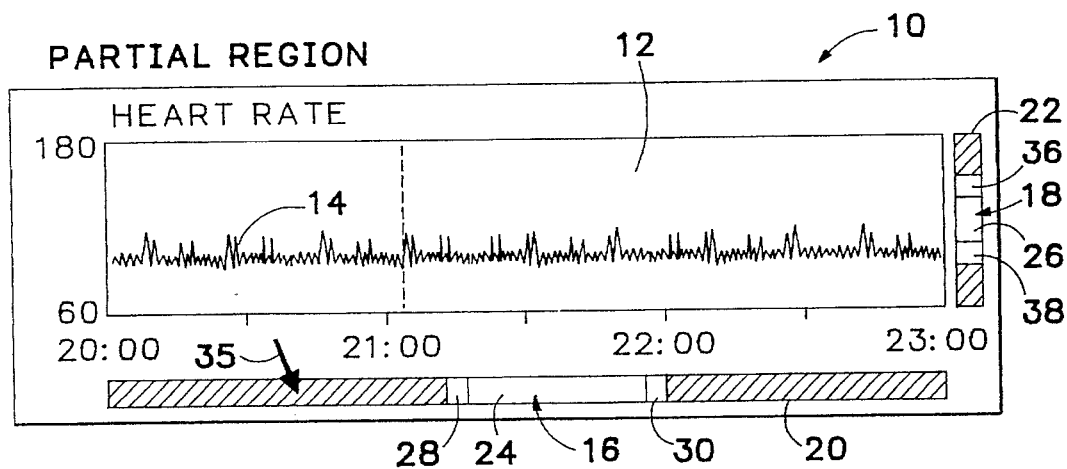
FIG. 1B illustrates a window having a selected region of the heart rate wave form of FIG. 1A displayed therein.

In FIG. 1A, display screen 10 includes a window 12 in which a continuous heart rate wave form 14 is displayed. ECG data (for example, data recorded with a Holter monitor) is stored in the system in which screen 10 is incorporated. The computer derives heart rate from the ECG data. Heart rate waveform 14 is referred to herein as a computer file or as a graphical image. In FIG. 1B, a scroll box 16 is bi-directionally movable along a horizontal scroll bar 20 while a scroll box 18 is bi-directionally movable along a vertical scroll bar 22.

Each scroll box includes a central portion, like central portions 24, 26 on scroll boxes 16, 18, respectively. Scroll box 24 includes a pair of end portions 28, 30 and scroll bar 18 includes upper and lower end portions 36, 38, respectively. The portions will be hereinafter referred to as "handles".

A conventional mouse or other cursor control device (not shown) controls the position of a cursor (also not shown) formed on the monitor under control of the computer. A switch or button on the mouse may be depressed by the user to effect certain control operations. One of the control operations is referred to herein as dragging. A scroll box is moved by positioning the cursor on to the central portion thereof, thereafter depressing the mouse button and holding it down while moving the cursor (by moving the mouse) generally along the axis of the scroll bar, like scroll bar 20, in the desired direction. Such action moves the scroll box synchronously with the cursor. As the cursor moves, that portion of the heart rate waveform displayed in window 12 also changes responsive to the cursor movement.

In the view of FIG. 1A, all of the data in the file is displayed, i.e. 24 hours worth of heart rate data in this example. The Holter recorder includes a clock which records the time of day of which each portion of the data is recorded. The time of day is displayed along the lower portion of window 12. For example, the label "20:00" shown in FIG. 1A indicates data acquired at 8:00 p.m. The file thus contains data acquired between 8:00 a.m. and the same time 24 hours later.

As can be seen, the range of the displayed portion of the waveform changes between FIG. 1A and FIG. 1B, with only three hours of the heart rate waveform being displayed in FIG. 1B. As used herein the term range indicates the size of the viewed portion of the graph in the units in which the graph is measured, i.e., the horizontal axis of FIG. 1A is arranged at 24 hours full scale and the horizontal axis of FIG. 1B is arranged at three hours full scale (20:00–23:00). The range is selected by the user by sizing the scroll box as described later.

Figure 1C:
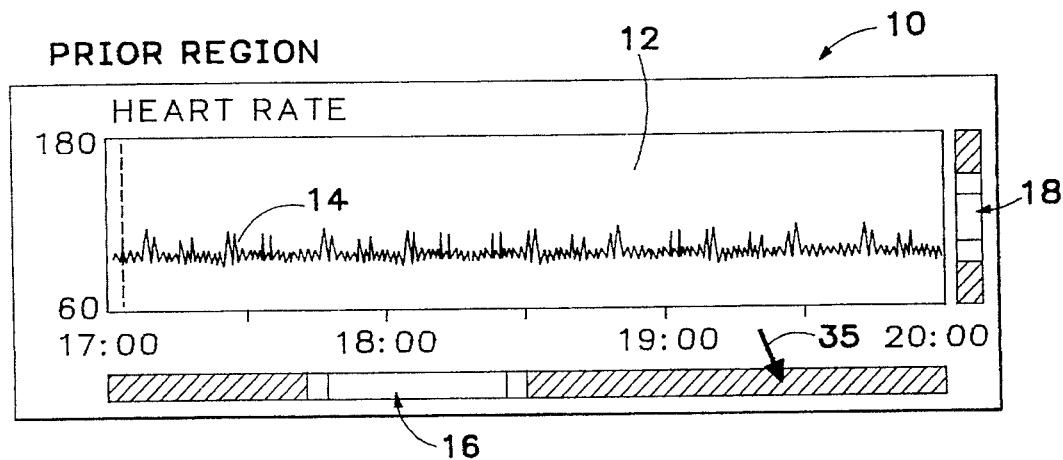
FIG. 1C illustrates a window displaying a Prior Region of the heart rate wave form of FIG. 1A relative to the selected region displayed in FIG. 1B.
Figure 1D:
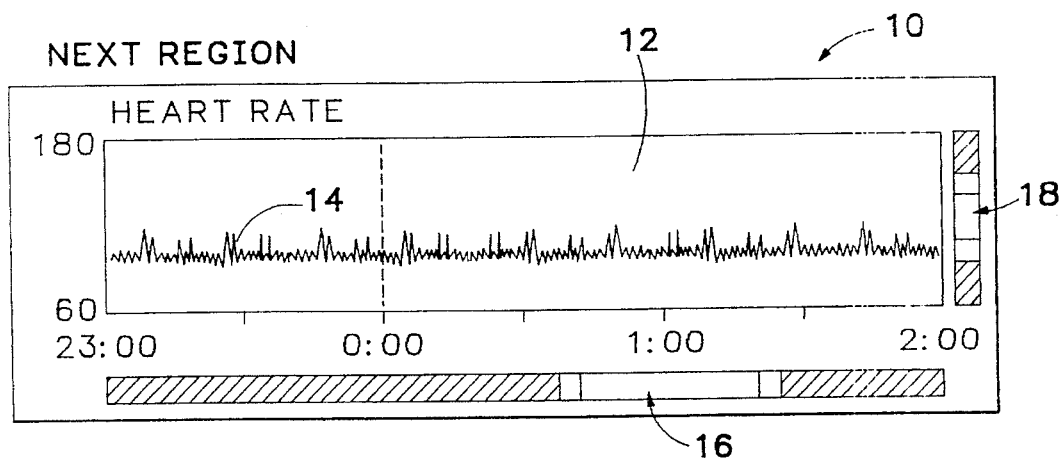
FIG. 1D illustrates a window displaying a Next Region of the heart rate wave form of FIG. 1A relative to the selected region of the wave form displayed in FIG. 1B.
Figure 2A:
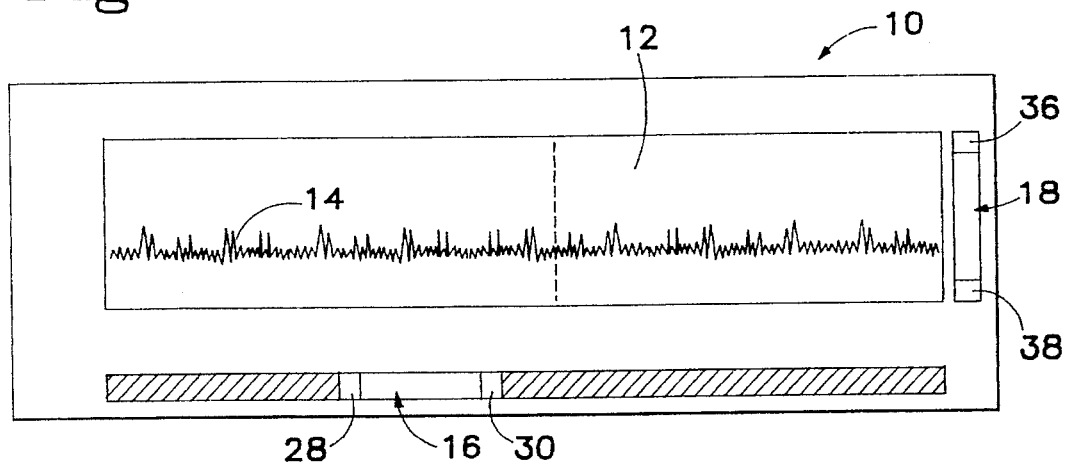
FIG. 2A illustrates a window that displays an alternative heart rate wave form image.
Figure 2B:
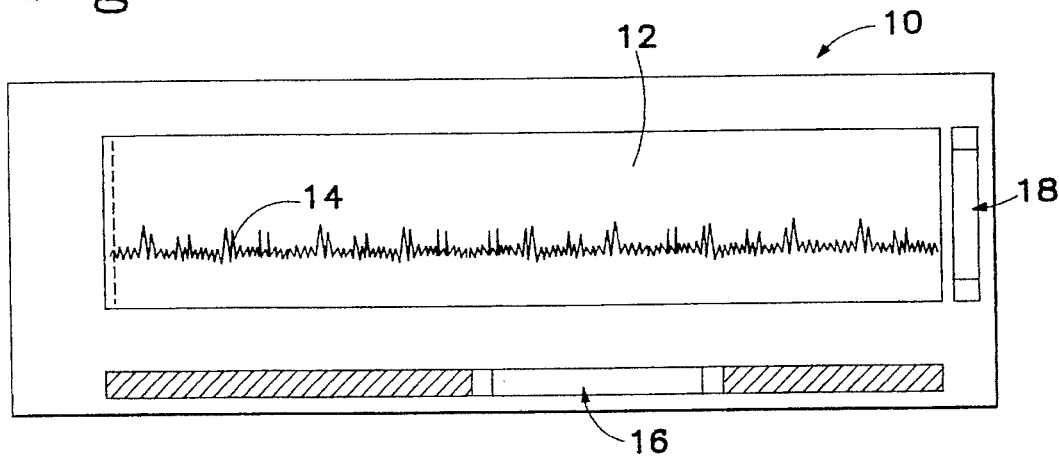
FIG. 2B illustrates a portion of the wave form image of FIG. 2A, the display having been "zoomed" to a scale or magnification factor greater than that employed in the display of FIG. 2A.
Figure 2C:
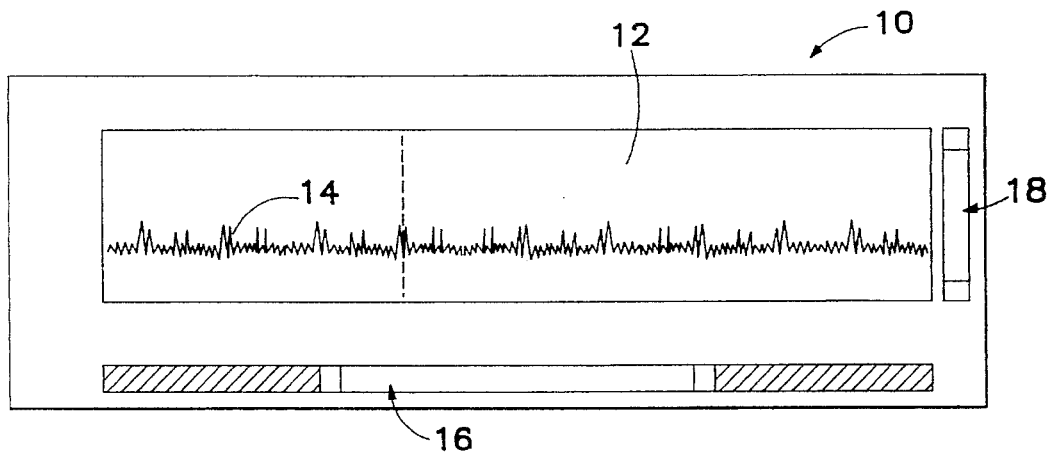
FIG. 2C illustrates a portion of the wave form image of FIG. 2A, the display having been "zoomed" to a scale or magnification factor less than the scale factor used in the display of FIG. 2B.
Figure 2D:
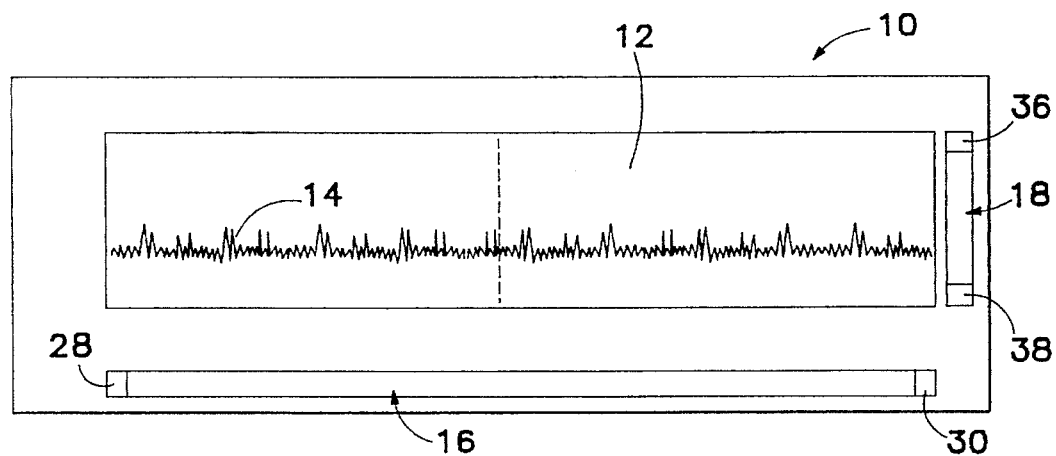
FIG. 2D illustrates the entire image file for the wave form image of FIG. 2A so that the scale or magnification factor is unity.

Referring to FIG. 1B, the next subsequent three-hour range of data can be viewed by positioning the cursor anywhere on scroll bar 20 to the right of horizontal scroll box 16 and clicking the mouse button. That portion is referred to herein as Next Region of the scroll bar. The result is shown in FIG. 1D (the data "wrapped around" to the beginning of the file). This procedure can be repeated to display subsequent three-hour sections of the waveform, or the mouse button held down to effect repeated movements of the scroll box.

A Prior Region can be viewed by clicking within that portion of the scroll bar 20 to the left of scroll box 16. For example, referring again to FIG. 1B, the range displayed is 20:00 (8:00 pm) to 23:00 (11:00 p.m.). To select the prior region, a cursor 35 is positioned within scroll bar 20 to the left of scroll box 16 and the mouse button is clicked. The result is shown in FIG. 1C, thus displaying the preceding three hours of the heart rate waveform. Referring to FIG. 1C, cursor 35 is positioned along scroll bar 20 to the fight of the scroll box 16. If the mouse button is clicked here, the result would be the next region, i.e. back to the display of FIG. 1B.

The horizontal range is selected by dragging handle 28 or handle 30 toward or away from the other end. For example, with respect to FIGS. 2A–2D, the range increases between the view of FIG. 2A and the view of 2B. Such is achieved by dragging scroll box handle 30 to the right. When handle 30 is so dragged, handle 28 remains stationary thereby lengthening the scroll box. Alternatively, the same effect may be achieved by dragging handle 28 to the left. When so dragged, the right end of the scroll box remains stationary, thereby shifting the range as indicated between FIGS. 2A and 2B. Similarly, the horizontal range is again expanded between FIGS. 2B and 2C in the same manner and again between 2C and 2D also in the same manner. As is the case with FIG. 1A, all of the data in the file illustrated in FIGS. 2A–2D is displayed in the view of FIG. 2D. Dragging a handle to change the length of the scroll box in a given dimension thus adjusts the scale of the displayed data in that dimension.

Consideration will now be given to the structure of a computer program which effects operation of display 10 as described above. In the present embodiment of the invention, the program was written using the Windows Software Development Kit Version 3.1 made by Microsoft Corporation of Redmond, Wash. Several of the function names referred to below are utilized by the Windows Software Development Kit and are well-known to persons having ordinary skill in the art.

The following is a description of an example of a software embodiment of the invention in a Windows operating environment. In this example, a graph controller (GC) is a windows control with properties similar to a scroll bar but with extended capabilities to facilitate the zoom and pan of a graph or picture as described above. The GC thus includes a central portion for position control and handles for scale control.

The following is a glossary of terms used in this description of a software embodiment:

Thumb: The moveable portion of the GC which corresponds to the portion of the file (data) being viewed. It can be sized by clicking and dragging on the ends or handles. The Thumb is referred to above as a scroll box (16 or 18 in FIG. 1).

Position: The position of the thumb is defined as the leftmost (or lowermost) part of the viewed part of the graph.

Range: The size of the viewed portion of the graph in the units in which the graph is measured. e.g. if the graph depicts years and the thumb goes from 1975 to 1990, the range of the GC is 15 years.

Increment: The smallest amount that the range and position can be changed. For example, a programmer may wish to set the increment to be 5 years. In this case, the range of the thumb can be 5, 10, 15 . . . years and the position of the thumb can be moved to 1960, 1965, 1970 . . .

Limits: The limits of a GC are the lowest and highest boundaries of the graph.

In general, in the software embodiment, all numbers dealing with position, range and limits of the GC are LONG type (32 bit) values. The range is always positive, and limits and position are signed. Horizontal GCs define their lower limit to be on the left. Vertical GCs define their lower limit to be on the bottom.

Graph controllers may be created and destroyed in the standard windows fashion. CreateWindow( . . . ) is called with a class-name of HGraphController for a horizontal control and VGraphController for a vertical one. The window-handle returned from CreateWindow( . . . ) is the handle to the GC. When created a GC has default parameter settings as follows: LowerLimit: 0, UpperLimit: 100, Position: 0, Range: 10. Destruction of a GC is also done in standard windows fashion by using DestroyWindow(hGC) where hGC is the window-handle returned from CreateWindow( . . . ).

In the software embodiment, a parent window sends configuration and status information to the graph controller (GC). The configuration messages are sent to the GC using the standard Windows SendMessage format (hDC, message, wParam, lParam). The configuration messages are described in the following Table 1:

TABLE 1

Graph Control Configuration Message Descriptions.

| Message Name and values | Description and interpretation |
| --- | --- |
| GC_SETPOS | sets the position of the thumb |
| wParam: FALSE | GC is not repainted |
| TRUE | GC is repainted |
| lParam: | new thumb position |
| GC_SETMIN | sets the lower limit of the GC |
| wParam: FALSE | GC is not repainted |
| TRUE | GC is repainted |
| lParam: | new GC lower limit |
| GC_SETMAX | sets the upper limit of the GC |
| wparam: FALSE | GC is not repainted |
| TRUE | GC is repainted |
| lParam: | new GC upper limit |
| GC_SETINC | sets the GC increment (this message could chang the range of the GC to force it to be a multiple of the increment). |
| wParam:FALSE | GC is not repainted |
| TRUE | GC is repainted |
| lParam: | new GC increment |
| GC_SETRANGE | sets the upper limit of the GC (the range is forced to be a multiple of the increment). |
| wParam: FALSE | GC is not repainted |
| TRUE | GC is repainted |
| lParam: | new GC range |

The following status messages (Table 2) are sent to the GC by the parent window using the standard windows SendMessage format (hDC, message, wParam, lParam). In all cases, wParam and lParam should be set to 0. The return value is the requested parameter.

TABLE 2

Graph Control Status Messages.

| Status Message | Returned Parameter |
| --- | --- |
| GC_GETPOS | current position of the thumb. |
| GC_GETMIN | current lower limit of the GC. |
| GC_GETMAX | current upper limit of the GC. |
| GC_GETINC | current increment of the GC. |
| GC_GETRANGE | current range of the thumb. |

The following event messages are sent by the GC to its parent to inform the parent about user interaction:

TABLE 3

User Interaction Event Message Descriptions.

| Event Message | Description |
| --- | --- |
| GC_NEWPOS | This message is sent after the user has changed the position of the thumb. |
| wParam: | Handle of the GC |
| lParam: | New Position |
| GC_NEWRANGE | This message is sent after the user has changed the size of the range. |
| wParam: | Handle of the GC. |
| lParam:if lParam > = 0 | New Range of the GC = lParam. Else see note 1. |
| GC_TRACK | This message is sent as the user is changing the position of the thumb (as opposed to GC_NEWPOS where the message is sent after the thumb is moved to indicate it's final resting place). This allows the application to update the graph dynamically. |
| wParam: | handle of GC |
| lParam: | current position |
| GC_TRACKRANGE | This message is sent as the user is changing the range of the thumb. |
| wParam: | Handle of the GC. |
| lParam:if lParam > = 0 | Current Range of the GC = lParam. Else see note 2. |
| GC_DBLCLICK | This message is sent if the user double clicks the mouse on the thumb. |
| wParam: | Handle of GC |
| lParam: | 0 |

Note 1: Else: New Range of the GC is –lParam and this message is the first of a two-message set (to be followed by a GC_NEWPOS message). Dragging the left side or bottom end) of the thumb thus causes both the range and the position to change.

Note 2: Else: Current Range of the GC is –lParam and this message is the first of a two-message set (to be followed by a GC_TRACK message). Dragging the left side or bottom end) of the thumb causes both the range and position to change.

Controller Internals

The parent window configures the GC using the configuration messages described above, and can query the GC's state using the status messages. The GC informs the parent window when the user has dragged the GC's thumb, "grown" the thumb or clicked on the next/prior regions. Using this information, the parent window can alter the display of the graph in some fashion which corresponds to the user's actions.

Graph Controller State

The "state" of the graph controller represents a complete description of the GC at any particular time. The state is maintained in a structure which is dynamically allocated; one per GC created so that every GC can have its own state independently. This structure is allocated in the WM_CREATE message using the LocalAlloc( ) function. The pointer to this structure is kept in the instance data of the window (the WinExtraBytes field in the WNDCLASS structure is set to size of(PGDESC)). The memory is deallocated during the WM_DESTROY message.

TABLE 4

Graph Controller Software State Variables.
(All dimensions are in logical units unless otherwise noted.)

| | |
|---|---|
| nMin | lower limit of the controller (corresponding to the leftmost or bottommost edge of the data, see the Glossary) |
| nMax | upper limit of the controller (corresponding to the rightmost or topmost edge of the data, see the Glossary). |
| nRange | current range of the thumb |
| nPos | current position of the thumb |
| nIncrement | current increment of the thumb |
| nMinThumbSize | minimum size of the thumb (in pixels). |
| nThumbWidth | width of the thumb (in pixels). Typically GC-2 |
| nUpDnSize | The size of the handles. Fixed to nThumbSize/4. |
| nUserState | An indication of what the user is currently doing to the thumb. It can have the following values: |
| IDLE | The user is not manipulating this GC. |
| INCUP | The user is clicking and holding in the "next region". |
| INCDOWN | The user is clicking and holding in the "prior region". |
| GROWUP | The user is moving the top/right handle of the thumb. |
| GROWDOWN | The user is moving the bottom/left handle. |
| TRACKING | The user is moving the thumb. |

Another state variable found to be useful is LastTrackingRect. This reflects the last position/size of the thumb during tracking operations to make painting the control easier. Yet another variable bHighLighted is a flag indicating whether the next/prior region is highlighted (so that the user can be given visual feedback the region has been clicked). To make the control usable, the physical size of the thumb must be large enough for the user to manipulate. It is permanently set to, for example, three times the width of a character in the default system font.

One of the most important elements in the GC is the transformation of device coordinates (pixels) into a coordinate system the programmer specifies (logical coordinates). Values such as the position and range of the thumb are specified in logical coordinates but displayed on the device at pixel locations (using the MM_TEXT mapping mode).

The size of the thumb is given by the following equation:

$$size=(GClength-nMinThumbSize)*(nRange-nInc)/(nMax-nMin-nInc)+nMinThumbSize$$

where GClength is the length of the GC in pixels, and the other variables come from the state structure of the GC described above (see Table 4). The thumbsize equation is applied to a typical application as follows. Assume the GC length is 1000 pixels, and the minimum thumbsize is 50 pixels. Accordingly, the first factor in the thumbsize equation equals 950 pixels. The heart rate data shown in the display windows of FIG. 1 and FIG. 2 represents data taken over a 24 hour period beginning at 8:00. Assuming that the range is set to 3 hours and the increment is one hour, the second factor of the thumbsize formula may be evaluated as $(3-1)(24-0-1)=2/23$ or 0.087. Finally, the minimum thumbsize, as noted, is 50. Accordingly, the thumbsize equals 950×0.087+50 which equals 133 pixels. These figures correspond to the scroll box (thumb) size in FIGS. 1B, 1C and 1D since the range is three hours in those illustrations.

Mapping the position of the thumb to a physical pixel location is done with the following equation. Note that the position of the thumb corresponds to it's leftmost (for a horizontal, or bottommost for a vertical controller) edge:

$$pos=(GClength-size)*(nPos-nMin)/(nMax-nMin-nRange)$$

where size is the thumb size from the above equation and GClength is the length of the GC in pixels. This equation is only valid for (nMax−nMin)!=nRange. If this is not the case (i.e. the range is equal to the extent of the GC) then the position is set to 0. Continuing the above example of an application having a 1000 pixel GC length, the thumb position is calculated as follows. The first factor in the thumb position formula is 1000−133=867, where 133 is the thumb size calculated above. The second factor of the thumb position formula is evaluated as the current logical position minus the minimum, i.e. 12−0=12 hours, divided by (24−0−3) or 21 hours, which equals $867 \times 12/21 = 495$. Thus, the left end of the horizontal thumb would be positioned at pixel position 495 for a display that starts at time 20:00 (i.e. 12 hours into the data file) and has a range of three hours.

Note that the physical thumb size is not proportional to the range because for small range values the thumb would be too small to be useful. Therefore, the physical thumb size is linear (but not proportional). When the range is nInc (the smallest value it can be) the physical size is nMinThumbSize. When the range is nMax−nMin the physical size is the length of the GC.

Painting the control (both the thumb and the background) is done on every movement of the thumb. The window class is specified as having a NULL background brush. This allows the handling of the WM_PAINT message to paint the entire control which reduces flashing and gives the illusion of a smoothly operating thumb. The colors of the thumb and background are obtained from windows with the GetSysColor( ) function. Highlights are added in the standard way to give the thumb a 3 dimensional look and feel. The function which handles the WM_PAINT message from Windows looks at the state variables in the GC to paint it in the correct fashion.

Responding to User Actions

A user can do any of the following actions with the GC: (1) Click on the next region; (2) Click on the prior region; (3) Grow the thumb fight (or up); (4) Grow the thumb left (or down); (5) Click in the middle of the thumb and move it (called tracking). The following describes what the GC does when each of these actions are performed.

Next Region

Action: user presses left mouse button down (1) set a timer for 0.2 seconds
(2) set state to IncUp
(3) set bHighLighted to TRUE
(4) repaint the GC
(5) Send the parent a GC_NEWPOS message informing it of the request for a new position (here the parent will usually set the new position by sending a GC_SETPOS message). The new position is nPos+nRange.

Action: user releases left mouse button (1) release the timer
(2) set state to Idle
(3) set bHighLighted to FALSE Action: timer messages are received do to the timer set when the left mouse button is pressed. This is so the user can click and hold the mouse and get repeated movements.

(1) Send the parent a GC_NEWPOS message informing it of the request for a new position (here the parent will usually set the new position by sending a GC₁₃SETPOS message). The new position is nPos+ nRange.

Prior Region

Action: user presses left mouse button down
(1) set a timer for 0.2 seconds
(2) set state to IncDown
(3) set bHighLighted to TRUE
(4) repaint the GC
(5) Send the parent a GC_NEWPOS message informing it of the request for a new position (here the parent will usually set the new position by sending a GC_SETPOS message). The new position is nPos+nRange.

Action: user releases left mouse button
(1) release the timer
(2) set state to IDLE
(3) set bHighLighted to FALSE Action: timer messages are received do to the timer set when the left mouse button is pressed. This is so the user can click and hold the mouse and get repeated movements.
(1) Send the parent a GC_NEWPOS message informing it of the request for a new position (here the parent will usually set the new position by sending a GC_SETPOS message). The new position is nPos+nRange.

Grow the Thumb Right (or up)

Action: user presses and holds the left mouse button on the fight (or top) handle
(1) set state to GrowUp
(2) set LastTackingRect to current thumb rectangle
(3) call DrawFocusRect( ) at LastTrackingRect location
(4) send a GC_TRACKRANGE message to the parent Action: user moves the mouse
(1) call DrawFocusRect( ) on the LastTrackingRect (this effectively erases the tracking rectangle)
(2) set LastTrackingRect to current thumb rectangle. The size of the rectangle is determined by the location of the mouse.
(3) send a GC_TRACKRANGE message to the parent Action: user releases the mouse button
(1) call DrawFocusRect0 on the LastTrackingRect (this effectively erases the tracking rectangle)
(2) send a GC_NEWRANGE message to the parent

Grow the Thumb Left (or down)

Action: user presses and holds the left mouse button on the left (or bottom) handle
(1) set state to GrowDown
(2) set LastTackingRect to current thumb rectangle
(3) call DrawFocusRect0 at LastTrackingRect location
(4) send a GC_TRACKRANGE message to the parent
(5) send a GC_TRACK message to the parent Action: user moves the mouse
(1) call DrawFocusRect0 on the LastTrackingRect (this effectively erases the tracking rectangle)
(2) set LastTrackingRect to current thumb rectangle. The size of the rectangle is determined by the location of the mouse.
(3) send a GC_TRACKRANGE message to the parent
(4) send a GC_TRACK message to the parent Action: user releases the mouse button
(1) call DrawFocusRect( ) on the LastTrackingRect (this effectively erases the tracking rectangle)
(2) send a GC_NEWRANGE message to the parent
(3) send a GC_NEWPOS message to the parent

Track the Thumb

Action: user presses and holds the left mouse button on middle of the thumb
(1) set state to Tracking
(2) set LastTackingRect to current thumb rectangle
(3) call DrawFocusRect0 at LastTrackingRect location
(4) send a GC_TRACK message to the parent Action: user moves the mouse
(1) call DrawFocusRect0 on the LastTrackingRect (this effectively erases the tracking rectangle)
(2) set LastTrackingRect to current thumb rectangle.
(3) send a GC_TRACK message to the parent Action: user releases the mouse button
(1) call DrawFocusRect0 on the LastTrackingRect (this effectively erases the tracking rectangle)
(2) send a GC_NEWPOS message to the parent Having illustrated and described the principles of our invention in a preferred embodiment thereof, it should be readily apparent to those skilled in the art that the invention can be modified in arrangement and detail without departing from such principles. We claim all modifications coming within the spirit and scope of the accompanying claims.

I claim:

1. A method for displaying a portion of a computer file comprising the steps of:
   displaying a selected portion of the file in a window having a scroll box on one side thereof for varying which portion of the file is displayed in the window;
   changing the length of the scroll box, in response to a user; and
   changing the scale of the displayed portion of the file proportional to and in response to the change in length of the scroll box.

2. The method of claim 1 wherein the step of changing the length of the scroll box is in response to the user dragging a first end of the scroll box with a cursor.

3. The method of claim 2 wherein the step of changing the length of the scroll box is additionally in response to the user dragging a second end of the scroll box with the cursor.

4. The method of claim 1 wherein said scroll box is bidirectionally movable along a linear path on one side of said window and wherein the step of changing the scale of the displayed portion of the file further comprises the step of changing the scale of the image along a direction parallel to said path.

5. The method of claim 4 wherein said window is rectangular and has a horizontal dimension and a vertical dimension and wherein the step of changing the scale of the image along a direction parallel to said path comprises the step of changing the vertical scale.

6. The method of claim 4 wherein said window is rectangular and has a horizontal dimension and a vertical dimension and wherein the step of changing the scale of the image along a direction parallel to said path comprises the step of changing the horizontal scale.

7. The method of claim 1 wherein the step of displaying the selected portion of the file in the window having the scroll box on one side thereof includes displaying the scroll box on a scroll bar.

8. A method for changing the scale and viewed portion of a graphical image comprising the steps of:

displaying a selected portion of the graphical image in a window on a monitor;

displaying a scroll box on one side of the window;

moving the scroll box, in response to a user;

changing the portion of the image displayed in the window responsive to scroll box movement;

changing the length of the scroll box, in response to the user; and changing the scale of the image displayed in the window responsive to the change in length of the scroll box.

9. The method of claim 8 wherein the step of moving the scroll box comprises the step of dragging a first end of the scroll box with a cursor.

10. The method of claim 8 wherein the step of changing the length of the scroll box comprises the step of dragging a first end of the scroll box with a cursor.

11. The method of claim 10 wherein the step of changing the length of the scroll box further comprises the step of maintaining a second end of the scroll box stationary during the step of dragging the first end of the scroll box with a cursor.

12. The method of claim 10 wherein the step of changing the length of the scroll box additionally comprises the step of dragging the second end of the scroll box with a cursor.

13. The method of claim 12 wherein the step of changing the length of the scroll box further comprises the step of maintaining the second end of the scroll box stationary during the step of dragging the first end of the scroll box with a cursor.

14. The method of claim 8 wherein said window is rectangular and has a horizontal dimension and a vertical dimension and wherein the step of changing the scale of the image comprises the step of changing the vertical scale.

15. The method of claim 8 wherein said window is rectangular and has a horizontal dimension and a vertical dimension and wherein the step of changing the scale of the image comprises the step of changing the horizontal scale.

16. The method of claim 8 wherein the step of displaying the scroll includes displaying the scroll box on a scroll bar.

17. Apparatus for viewing a graphical image comprising:

means for displaying a window on a monitor;

means for displaying a selected portion of the image in the window;

means for displaying a scroll box on one side of the window;

means for changing the length of the scroll box in response to a user;

means for changing the scale of the image displayed in the window responsive to the change in the length of the scroll box.

18. The apparatus of claim 17 wherein said scroll box includes a visually defined end portion and wherein said means for changing the length of the scroll box comprises means for dragging the end portion.

19. The apparatus of claim 18 wherein said means for dragging the end portion comprises means for displaying a cursor on said screen and means for moving said cursor.

20. The apparatus of claim 17 wherein said apparatus further includes means for moving said scroll box.

21. The apparatus of claim 20 wherein said apparatus further includes means for changing the displayed portion of the image responsive to scroll box movement.

22. The apparatus of claim 20 wherein said means for moving the scroll box includes means for calculating a size of the scroll box and means for determining a position of the scroll box responsive to a user dragging an end of the scroll box.

23. The apparatus of claim 17 wherein the means for displaying the scroll box displays the scroll box on a scroll bar.

* * * * *